Jan. 17, 1939. R. C. MURPHEY Plant Pat. 310
CHRYSANTHEMUM
Filed Dec. 4, 1937
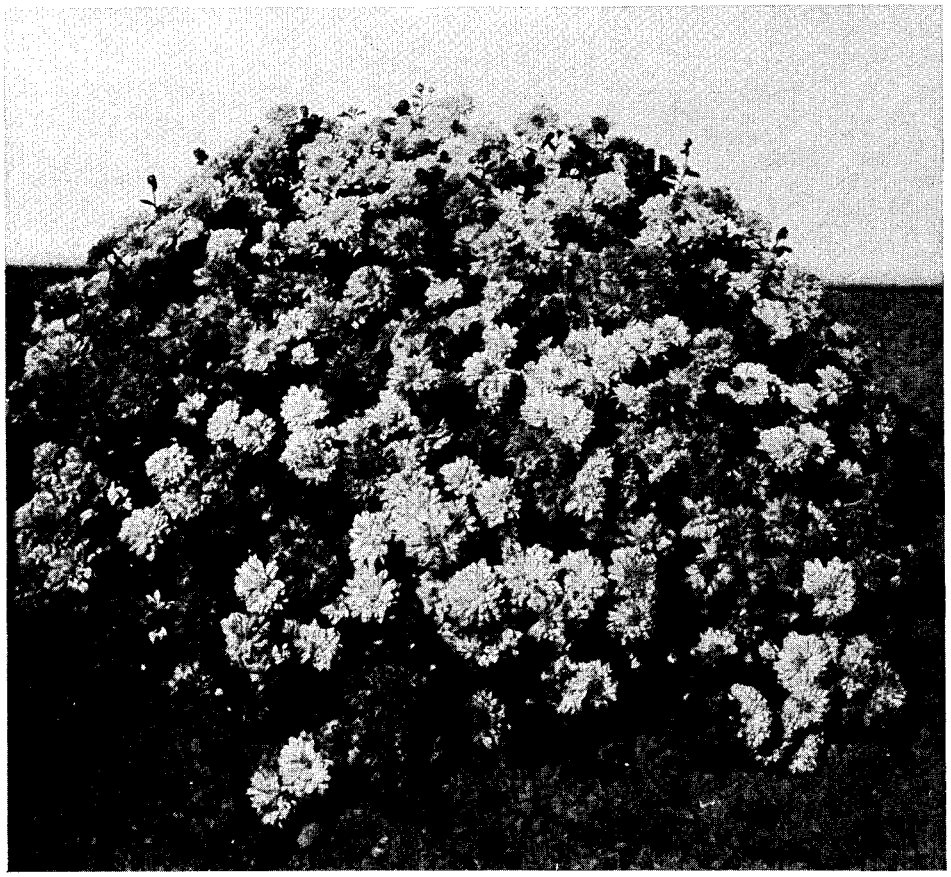
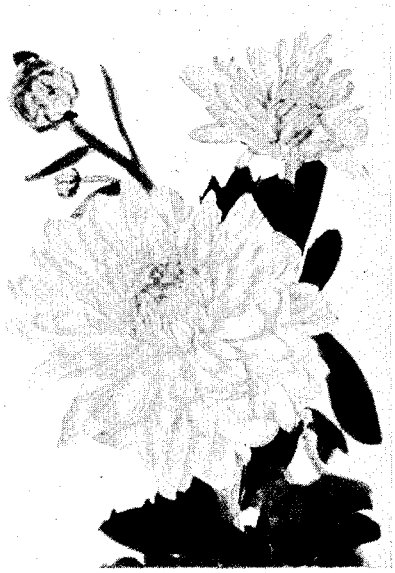
Inventor
ROBERT C. MURPHEY.
By Robb & Robb
Attorneys Patented Jan. 17, 1939

Plant Pat. 310

UNITED STATES PATENT OFFICE

310

CHRYSANTHEMUM

Robert C. Murphey, Urbana, Ohio, assignor to R. H. Murphey's Sons Company, Urbana, Ohio Application December 4, 1937, Serial No. 178,154

1 Claim. (Cl. 47—60)

This invention relates to a novel and distinct variety of chrysanthemum plant which has been found to be highly desirable for use in group and border planting because of its size, form, and habits of growth. The shape and color of the flowers additionally lend themselves to increasing the desirability of the plant, both from the standpoint of their adaptability for group and border plantings, and their individual attractiveness.

The new variety is dwarf and compact in form, a profuse bloomer, the flowers being arranged quite close together and the plant growing in such a manner as to present a substantially flat top.

My new variety was produced by hybridization. A pink chrysanthemum, known as Azaleamum, was crossed with an Aladdin chrysanthemum, the new variety herein described being a seedling of the parents just named.

While my new variety exhibits characteristics of both parents, it has others resembling neither. Its foliage is similar to that of Aladdin. In habit of growth, on the other hand, my new variety resembles Azaleamum, especially with regard to the dwarfness and compactness of the plant and its trait of profuse blooming such that the outer extremities, especially at the top, are covered with flowers growing very close together.

As distinguishing, however, from Azaleamum, which is spheroidal or mound-like in form, the blooms of my new variety grow so as to produce the effect of a comparatively flat surface. In view of this tendency of the blooms to grow evenly across the top of the plant, and because the lateral shoots do bloom at the sides, rounding the plants to some extent at the sides, the habit of growth of my new variety may be described as semi-spheroidal, as distinguished from the term spheroidal, applicable to Azaleamum.

Another distinctive characteristic of my new variety is its habit of blooming earlier than many other varieties of chrysanthemum. Terminal buds bloom about September 5th, in the region of Urbana, Ohio. Lateral buds bloom ten days to two weeks later. The blooming period lasts about five weeks, depending on the weather in the meantime. No artificial methods were used to hasten blooming, so that the above dates are of the natural blooming time in the region mentioned.

The plants of my new variety ordinarily grow to a height of about twelve inches and are about two and one-half feet across when fully grown.

My new variety of chrysanthemum plant has been found to maintain its distinctive characteristics through succeeding generations when asexually reproduced, being propagated from cuttings.

*Description*

Type:
- Hardy; dwarf; outdoors; seedling; for garden decoration or pot plant.

Flower:
- *Locality where grown.*—Urbana, Ohio.
- *Flowers borne.*—Many to stem; in cluster; on medium stems.
- *Quantity of bloom.*—Abundant; outdoors.
- *Continuity.*—Continuous.

Bud:
- Before calyx breaks:
  - *Size.*—Medium.
  - *Form.*—Globular.
- As calyx breaks:
  - *Color* (compared with Maerz & Paul Dictionary of color tables).—Dark cardinal (Plate 6 L 8).
- As first petal opens:
  - *Size.*—Medium.
  - *Form.*—Globular.
  - *Color.*—(Plate 5 I 10.)
  - *Opening.*—Opens up well, double to the center.

Bloom:
- *Size when fully open.*—Medium; one and one-half to two inches.
- *Petalage.*—Double, arranged regularly.
- *Form.*—Pompom.

Petals:
- Soft.
- *Shape.*—Oval.
- *Average number to flower.*—About 205.

Plant:
- *Foliage.*—Abundant, medium, heavy.
- *Color.*—Upper surface—green (Plate 24 L 3). Under surface—green (Plate 31 A 7).
- *Disease.*—Resistant to mildew, blackspot.

Growth:
- Dwarf, bushy, vigorous.

Color:
- *Outside surface.*—Acacia (Plate 11 K 1), overlaid primarily in center of petal with dark cardinal (Plate 6 L 8) to form a mottled shade of approximately Plate 1 E 11.
- *Inside surface.*—Chrome lemon (Plate 9 K 2), slightly overlaid with dark cardinal (Plate 6 L 8) on extreme tip and outer edge.

(Above description made when flower newly and fully opened.)

I claim:

A new and distinct variety of chrysanthemum plant as shown and described, characterized by its novelty in reference to the color of the flower and the habit of growth of the plant.

ROBERT C. MURPHEY